(12) United States Patent
Sekikawa

(10) Patent No.: US 9,610,067 B2
(45) Date of Patent: Apr. 4, 2017

(54) BIOPSY NEEDLE

(71) Applicant: OLYMPUS CORPORATION, Hachioji-shi, Tokyo (JP)

(72) Inventor: Tomohiro Sekikawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/252,997

(22) Filed: Aug. 31, 2016

(65) Prior Publication Data

US 2016/0367232 A1    Dec. 22, 2016

Related U.S. Application Data

(63) Continuation of application No. PCT/JP2015/075723, filed on Sep. 10, 2015.

(30) Foreign Application Priority Data

Feb. 19, 2015    (JP) .................................. 2015-030449

(51) Int. Cl.
*A61B 10/00*    (2006.01)
*A61B 10/04*    (2006.01)
(Continued)

(52) U.S. Cl.
CPC .............. *A61B 10/04* (2013.01); *A61B 1/018* (2013.01); *A61B 8/12* (2013.01); *A61B 8/4416* (2013.01);
(Continued)

(58) Field of Classification Search
CPC .......................... A61B 5/3286; A61B 17/3417
(Continued)

(56) References Cited

U.S. PATENT DOCUMENTS 3,090,384 A * 5/1963 Baldwin ............. A61M 5/3286
604/272
7,070,583 B1 * 7/2006 Higuchi ............. A61M 5/3286
604/164.06
2009/0318946 A1   12/2009 Tamesada

FOREIGN PATENT DOCUMENTS

JP    H09-504979 A    5/1997
JP    H10-57490 A    3/1998
(Continued)

OTHER PUBLICATIONS

Dec. 1, 2015 International Search Report issued in International Patent Application No. PCT/JP2015/075723.

*Primary Examiner* — Max Hindenburg
*Assistant Examiner* — Jonathan M Foreman
(74) *Attorney, Agent, or Firm* — Oliff PLC

(57) ABSTRACT

A needle tip section of a biopsy needle includes a first beveled surface having a plane extended across a tube axis of a tubular section, a second beveled surface adjacent to and forming an angle with the first, having a plane adjacent to an inner circumferential surface of the tubular section, a third beveled surface adjacent to and forming an angle with the first beveled surface, opposite the second, with an opening portion interposed therebetween and having a plane adjacent to the inner circumferential surface of the tubular section, a first boundary line between the first and second beveled surfaces, and a second boundary line between the first and third beveled surfaces, and the first and second boundary lines are non-parallel straight lines having an interval that gradually increases in a direction from the second toward the first end portion in a tube axis direction of the tubular section.

7 Claims, 12 Drawing Sheets

(51) Int. Cl.
  *A61B 10/02* (2006.01)
  *A61B 1/018* (2006.01)
  *A61B 8/12* (2006.01)
  *A61B 8/00* (2006.01)
  *A61M 5/32* (2006.01)

(52) U.S. Cl.
  CPC .......... *A61B 8/463* (2013.01); *A61B 10/0275* (2013.01); *A61M 5/3286* (2013.01); *A61B 2010/045* (2013.01)

(58) Field of Classification Search
  USPC ........................................ 600/562, 564, 567
  See application file for complete search history.

(56) References Cited

FOREIGN PATENT DOCUMENTS

| | | |
|---|---|---|
| JP | 2008-154842 A | 7/2008 |
| JP | 2011-000214 A | 1/2011 |
| JP | 3187362 U | 11/2013 |
| WO | 95/24858 A1 | 9/1995 |
| WO | 2007/142098 A1 | 12/2007 |

\* cited by examiner

BIOPSY NEEDLE

This application is a continuation application, based on PCT/JP2015/075723, filed on Sep. 10, 2015, claiming priority based on Japanese Patent Application No. 2015-030449, filed in Japan on Feb. 19, 2015, the content of which is incorporated herein by reference.

FIELD OF THE INVENTION

The present invention relates to a biopsy needle.

DESCRIPTION OF THE RELATED ART

In the related art, medical needles having various needle point shapes are known. For example, Japanese Unexamined Patent Application, First Publication No. H10-057490 discloses a injection needle having a needle point shape constituted of a plurality of surfaces and capable of reducing pain during injection. In addition, Japanese Unexamined Patent Application, First Publication No. 2011-000214 discloses a biopsy needle body including a needle point structure capable of supplying a cooling gas to tissue in order to limit damage to the tissue serving as a biopsy target. As a needle point shape that seems to be effective in increasing the collected amount of tissue, a Menghini type needle machined such that a sharp blade is formed throughout a circumference of a needle point opening as disclosed in Japanese Unexamined Patent Application, First Publication No. 2008-154842 is known.

SUMMARY OF THE INVENTION

Means for Solving the Problem

An aspect of the present invention is a biopsy needle including: a tubular section formed in a hollow tube shape and having a first end portion in a tube axis direction and a second end portion opposite thereto; and a needle tip section having an opening portion in communication with the inside of the tubular section and formed at a position including the first end portion of the tubular section, wherein the needle tip section includes: a first beveled surface constituted of a plane extended in a direction crossing a tube axis of the tubular section and configured to define a part of a contour of the opening portion; a second beveled surface adjacent to the first beveled surface and forming an angle with the first beveled surface, constituted of a plane adjacent to an inner circumferential surface of the tubular section, and configured to define a part of the contour of the opening portion using a nodal line between the inner circumferential surface and the second beveled surface; a third beveled surface adjacent to the first beveled surface and forming an angle with the first beveled surface at an opposite side of the second beveled surface with the opening portion interposed therebetween, constituted of a plane adjacent to the inner circumferential surface of the tubular section, and configured to define a part of the contour of the opening portion using a nodal line between the inner circumferential surface and the third beveled surface; a first boundary line serving as a boundary between the first beveled surface and the second beveled surface; and a second boundary line serving as a boundary between the first beveled surface and the third beveled surface, and the first boundary line and the second boundary line are non-parallel straight lines having an interval that gradually increases in a direction from the second end portion toward the first end portion in the tube axis direction of the tubular section.

In a cross section crossing the nodal line between the second beveled surface and the inner circumferential surface in a cross section perpendicular to the tube axis of the tubular section, an angle formed between the second beveled surface and the inner circumferential surface may be constantly less than 90°, and in a cross section crossing the nodal line between the third beveled surface and the inner circumferential surface and perpendicular to the tube axis of the tubular section, an angle formed between the third beveled surface and the inner circumferential surface may be constantly less than 90°.

The opening portion may include a first opening end portion that configures the contour of the opening portion at a position closest to the first end portion in the tube axis direction of the tubular section; and a second opening end portion that configures the contour of the opening portion at a position closest to the second end portion in the tube axis direction of the tubular section, and a cross section perpendicular to the tube axis of the tubular section through a middle point of a line segment that connects the first opening end portion and the second opening end portion may cross the nodal line between the second beveled surface and the inner circumferential surface and the nodal line between the third beveled surface and the inner circumferential surface.

In the cross section perpendicular to the tube axis of the tubular section through the middle point of the line segment that connects the first opening end portion and the second opening end portion, the angle formed between the second beveled surface and the inner circumferential surface may be less than 70°, and in the cross section perpendicular to the tube axis of the tubular section through the middle point of the line segment that connects the first opening end portion and the second opening end portion, the angle formed between the third beveled surface and the inner circumferential surface may be less than 70°.

In the cross section crossing the nodal line between the second beveled surface and the inner circumferential surface and perpendicular to the tube axis of the tubular section, the angle formed between the second beveled surface and the inner circumferential surface may be constantly less than 70°, and in the cross section crossing the nodal line between the third beveled surface and the inner circumferential surface and perpendicular to the tube axis of the tubular section, the angle formed between the third beveled surface and the inner circumferential surface may be constantly less than 70°.

The biopsy needle of the aspect may further have a fourth beveled surface constituted of a plane configured to define a part of the contour of the opening portion at a position closer to the second end portion than the first beveled surface, adjacent to the second beveled surface and the third beveled surface, and disposed between the second beveled surface and the third beveled surface.

The needle tip section may have a side hole formed at an outer circumferential surface of the tubular section of an opposite side of the first beveled surface and in communication with the inside of the tubular section.

DETAILED DESCRIPTION OF THE INVENTION

Figure 1:
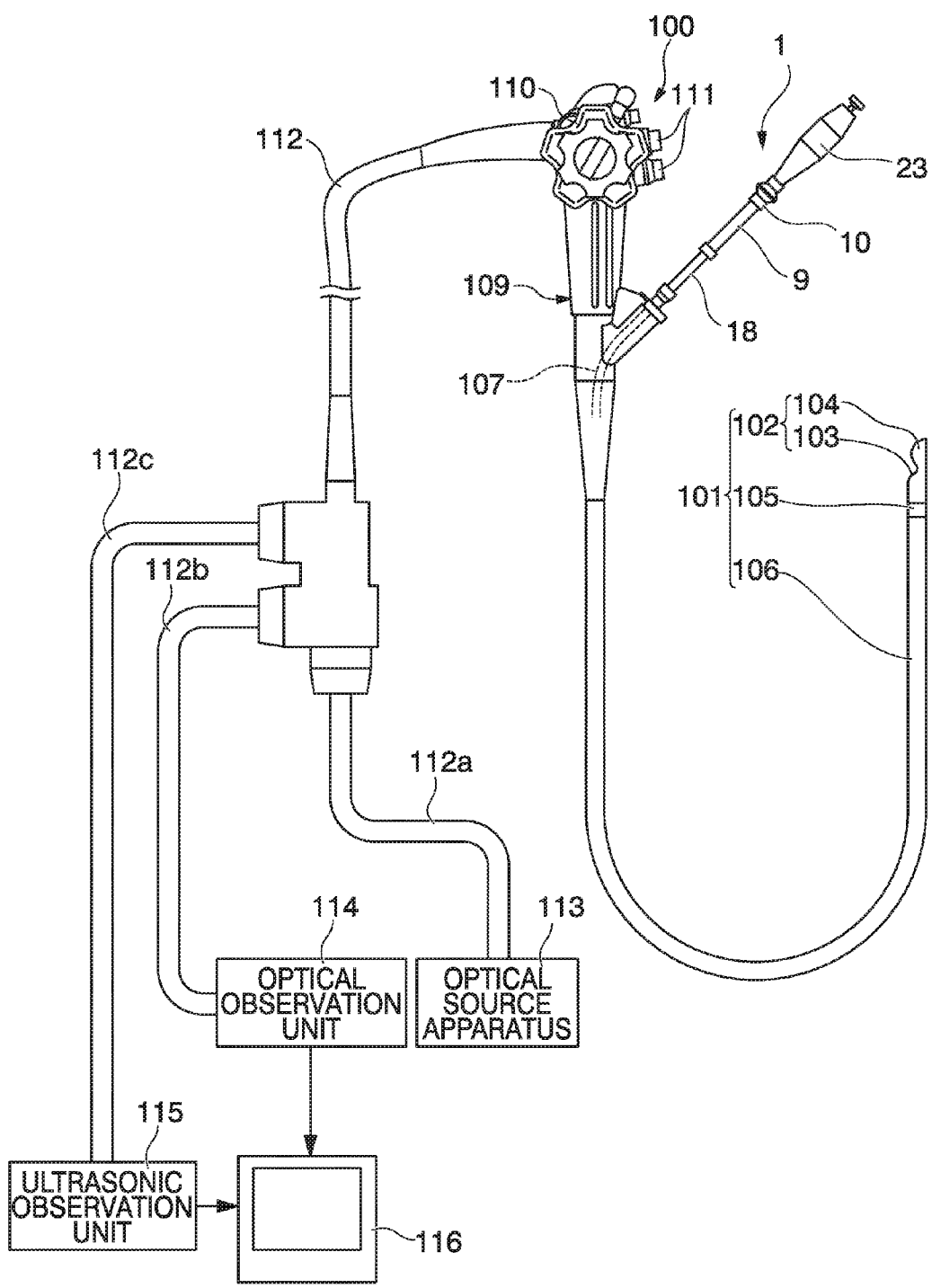
FIG. 1 is a general view showing a state in which a biopsy needle of an embodiment of the present invention is attached to an ultrasonic endoscope.
Figure 2:
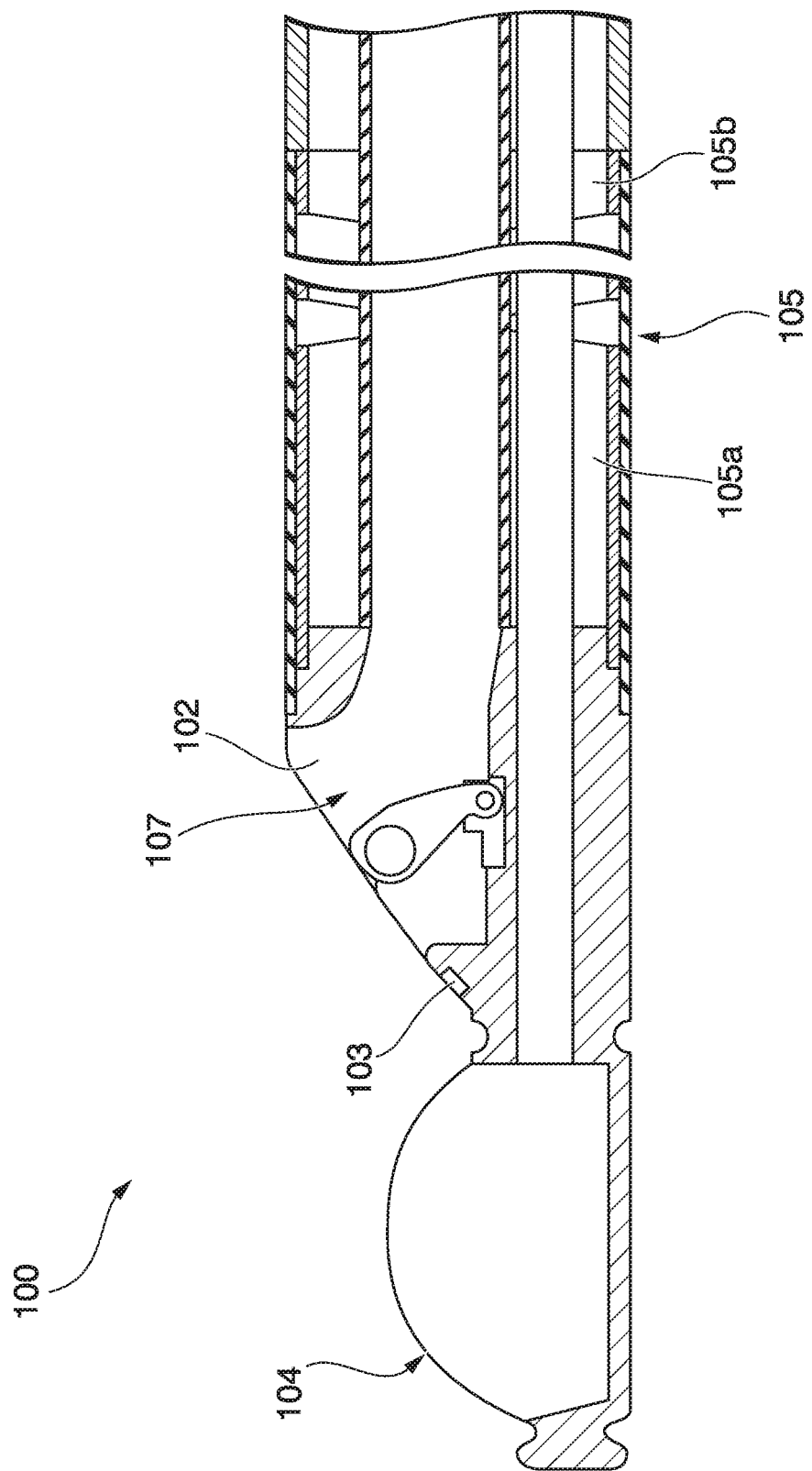
FIG. 2 is a cross-sectional view of a distal portion of the ultrasonic endoscope.

An embodiment of the present invention will be described. FIG. 1 is a general view showing a state in which a biopsy needle of the embodiment is attached to an ultrasonic endoscope. FIG. 2 is a cross-sectional view of a distal portion of the ultrasonic endoscope.

A biopsy needle 1 for an endoscope of the embodiment shown in FIG. 1 (hereinafter referred to as "the biopsy needle 1") is a biopsy needle serving as a part of a biopsy system and is combined with an ultrasonic endoscope 100 to be used in a biopsy.

First, an example of the endoscope used with the biopsy needle 1 of the embodiment will be described. Further, a configuration of the endoscope that can be used with the biopsy needle 1 of the embodiment is not particularly limited.

The ultrasonic endoscope 100 includes an insertion section 101 inserted into a body from a distal end thereof, an operation section 109 attached to a proximal end of the insertion section 101, a universal cord 112 having a first end connected to a side portion of the operation section 109, a light source apparatus 113 connected to a second end of the universal cord 112 via a branch cable 112a, an optical observation unit 114 connected to the second end of the universal cord 112 via a branch cable 112b, and an ultrasonic observation unit 115 connected to the second end of the universal cord 112 via a branch cable 112c.

The insertion section 101 has a distal hard section 102, a bendable section 105, and a flexible tube section 106 that are formed sequentially from a distal side thereof.

The distal hard section 102 includes an optical imaging mechanism 103 configured to perform optical observation, and an ultrasonic scanning mechanism 104 configured to perform ultrasonic observation.

The optical imaging mechanism 103 includes various constitutions that are not shown, such as an imaging optical system in which a field of vision is directed toward an inclined forward side of the distal hard section 102, an image sensor such as a CCD, a CMOS, or the like, configured to detect an image of a subject that enters through the imaging optical system, and a CPU or the like configured to control an operation of the image sensor.

The ultrasonic scanning mechanism (a probe) 104 includes an ultrasonic vibrator (not shown) configured to emit and receive ultrasonic waves. The ultrasonic waves which are emitted from the ultrasonic vibrator, hit an observation target, and reflected off the target are received by the ultrasonic vibrator of the ultrasonic scanning mechanism 104. The ultrasonic scanning mechanism 104 outputs a signal to the ultrasonic observation unit 115 based on the ultrasonic waves received by the ultrasonic vibrator. The ultrasonic scanning mechanism 104 of the embodiment is used to acquire an ultrasonic wave image of the tissue serving as the biopsy target and acquire an ultrasonic wave image of a needle tube 3 in a process of the biopsy procedure.

The bendable section 105 is formed in a tubular shape. The bendable section 105 is bent in a predetermined direction by pulling an angle wire (not shown) fixed to a distal end 105a (see FIG. 2) of the bendable section 105 and extending to the operation section 109 in the operation section 109. The bendable section 105 of the embodiment can be bent in two directions corresponding to a scanning direction of ultrasonic waves.

In the embodiment, for example, while the endoscope having a small outer diameter of the insertion section and bendable in two directions is used for treatment of a respiratory organ, when treatment of, for example, a digestive organ is performed, an endoscope having a large outer diameter and that is bendable in four direction with a high degree of manipulation freedom may also be used.

The flexible tube section 106 is a tubular member fixed to a proximal end 105b of the bendable section 105. The flexible tube section 106 is flexibly formed such that the distal hard section 102 can be guided to a predetermined position in the lumen tissue or the body cavity.

A channel 107 through which the biopsy needle 1 is inserted and a pipe line (not shown) configured to perform air supply, water supply, suction, or the like, are disposed in the bendable section 105 and the flexible tube section 106, respectively.

A first end (a distal end) of the channel 107 is opened in the vicinity of the distal portion of the distal hard section 102, and a second end (a proximal end) of the channel 107 is opened at a side surface of a distal side of the operation section 109. A proximal port member formed in a flange shape is fixed to the second end (the proximal end) of the channel 107. The biopsy needle 1 used with the ultrasonic endoscope 100 can be fixed to the proximal port member.

The operation section 109 shown in FIG. 1 has an outer surface formed such that an operator who uses the ultrasonic endoscope 100 can hold the operation section 109 with his/her hand. Further, the operation section 109 includes a bending operation mechanism 110 configured to pull the angle wire to bend the bendable section 105, and a plurality of switches 111 configured to perform air supply, water supply or suction through the pipe line.

The light source apparatus 113 is an apparatus configured to emit illumination light for imaging using the optical imaging mechanism 103.

The optical observation unit 114 is configured to project pictures imaged by the image sensor of the optical imaging mechanism 103 on a monitor 116.

The ultrasonic observation unit 115 is configured to receive a signal output from the ultrasonic scanning mechanism 104 and generate the image based on the signal to project the image on the monitor 116.

Figure 3:
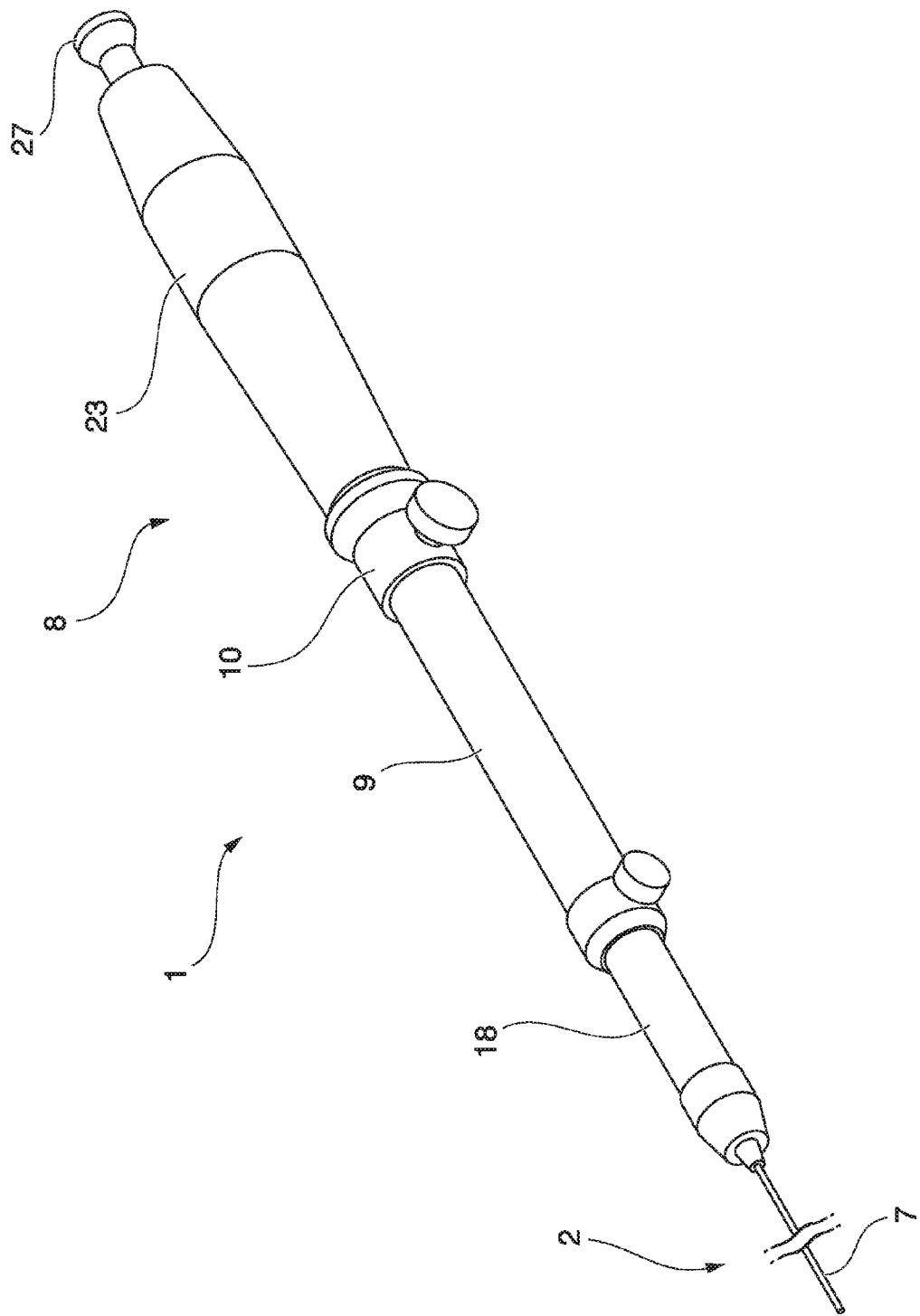
FIG. 3 is a perspective view of the biopsy needle.

A configuration of the biopsy needle 1 will be described. FIG. 3 is a perspective view of the biopsy needle 1.

As shown in FIGS. 1 and 3, the biopsy needle 1 includes an insertion body 2 inserted into a body, a manipulation section (a treatment tool manipulation section) 8 configured to manipulate the insertion body 2, and a stylet (a cored bar) 27.

The insertion body 2 is a long member that can be attached to the channel 107 that can protrude from the distal end of the insertion section 101 of the ultrasonic endoscope 100. The insertion body 2 includes the needle tube 3 and a tubular sheath 7 through which the needle tube 3 is inserted.

A configuration of the needle tube 3 of the biopsy needle 1 of the embodiment will be described in detail.

Figure 4:
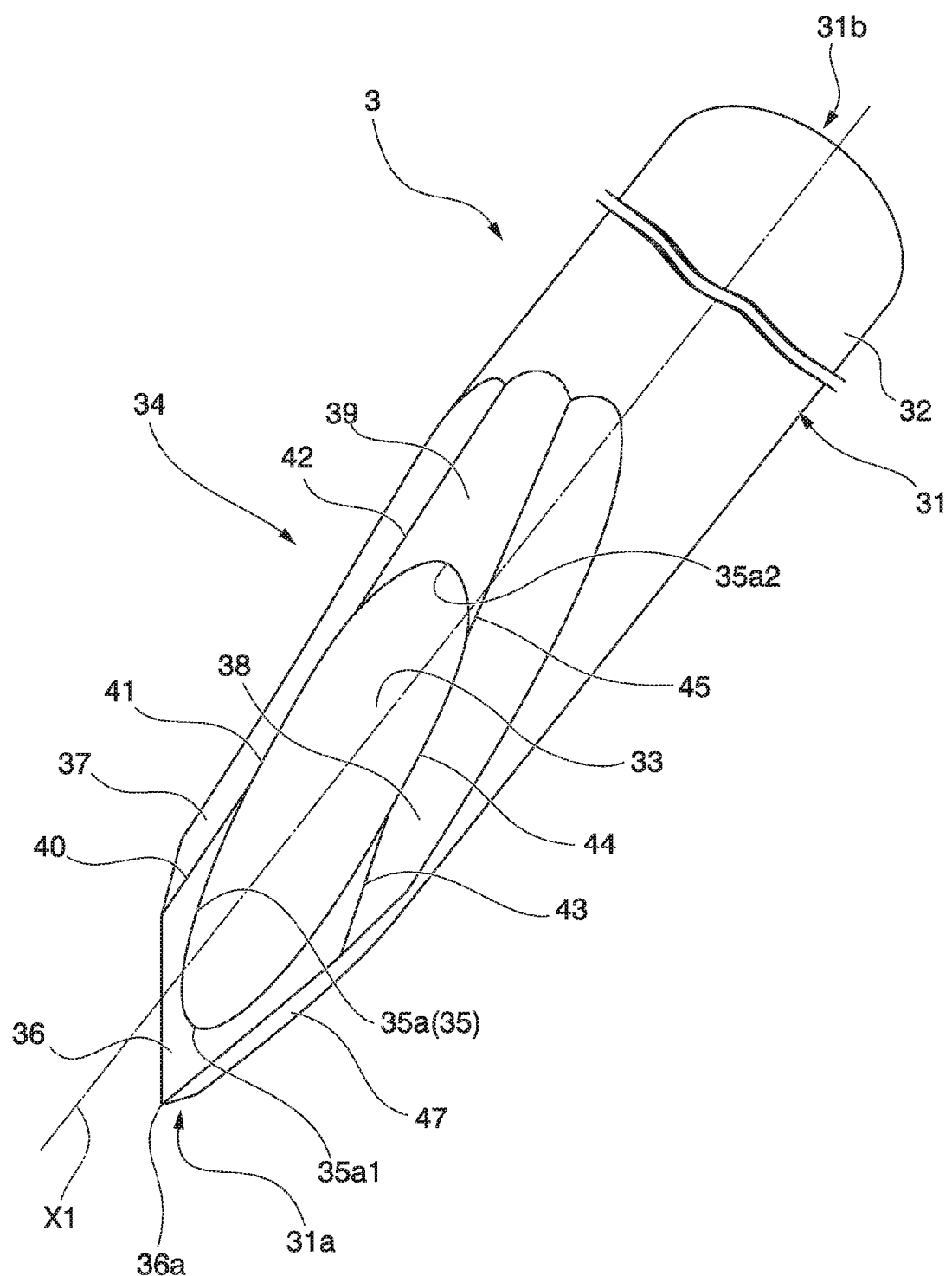
FIG. 4 is a perspective view showing a needle tube of the biopsy needle.
Figure 5:
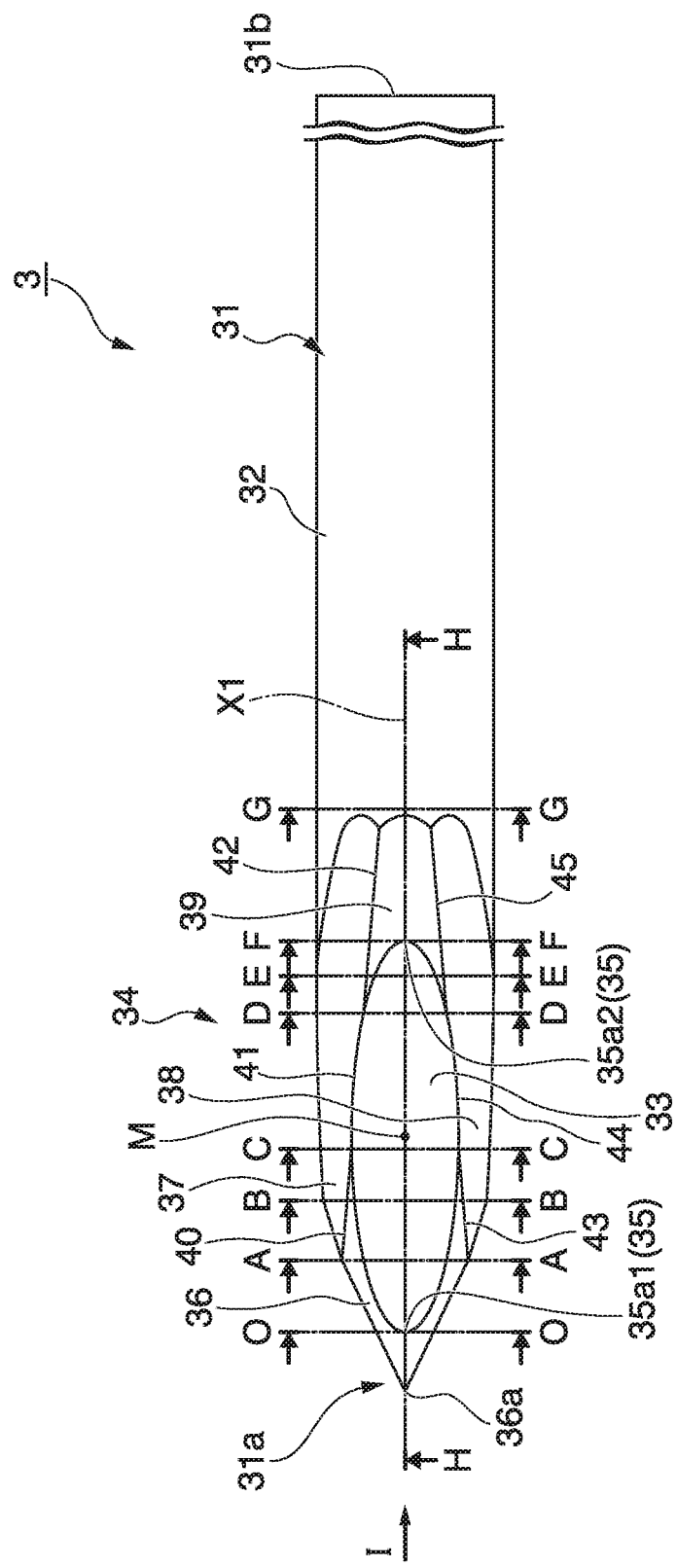
FIG. 5 is a plan view of the needle tube.
Figure 6:
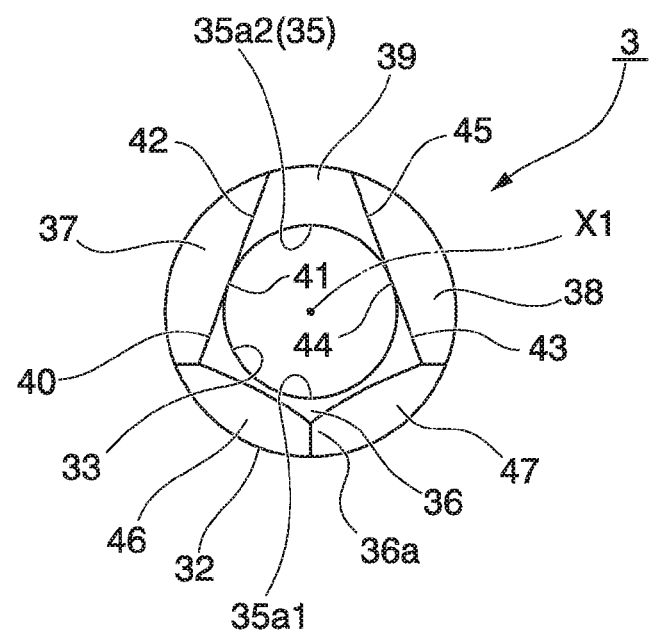
FIG. 6 is a front view of the needle tube.
Figure 7:
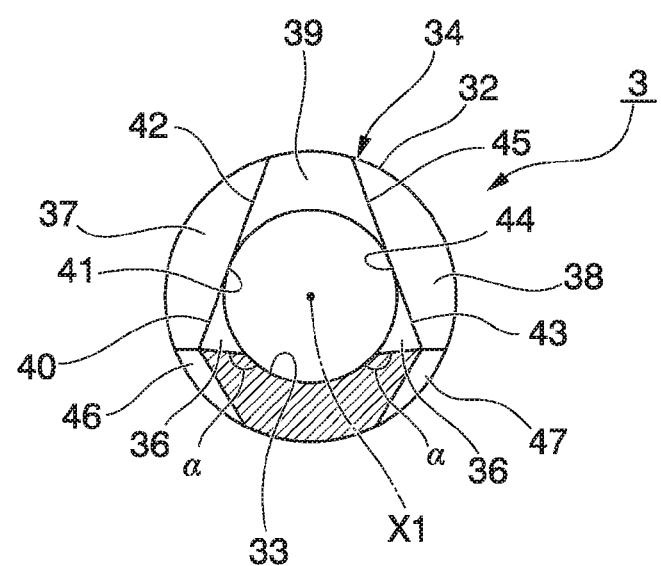
FIG. 7 is a cross-sectional view taken along line A-A of FIG. 5.
Figure 8:
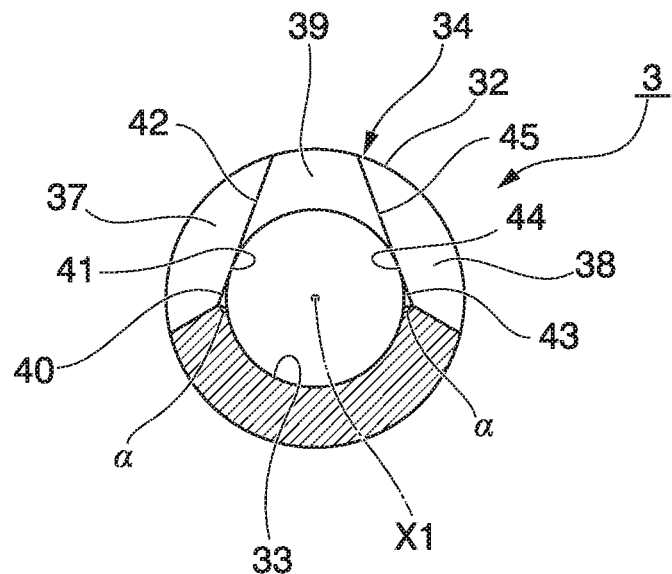
FIG. 8 is a cross-sectional view taken along line B-B of FIG. 5.
Figure 9:
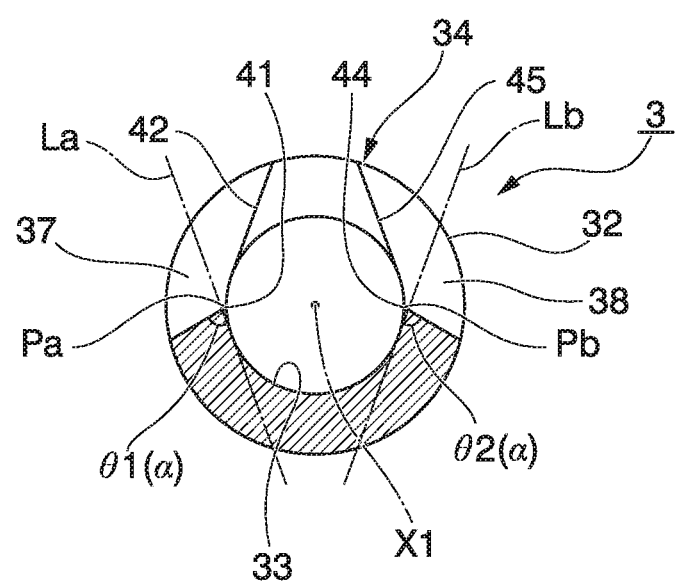
FIG. 9 is a cross-sectional view taken along line C-C of FIG. 5.
Figure 10:
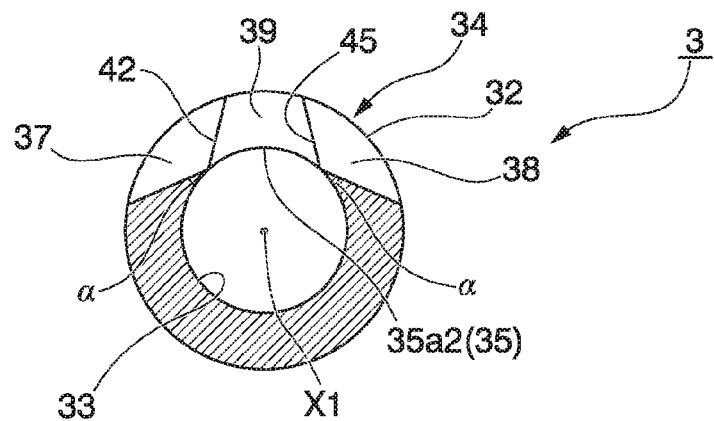
FIG. 10 is a cross-sectional view taken along line D-D of FIG. 5.
Figure 11:
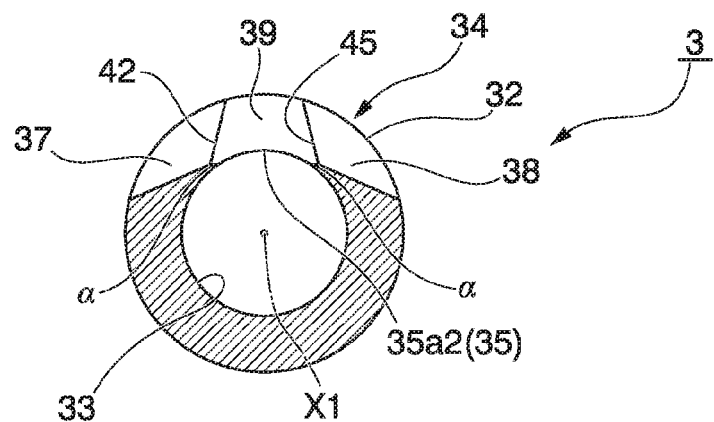
FIG. 11 is a cross-sectional view taken along line E-E of FIG. 5.
Figure 12:
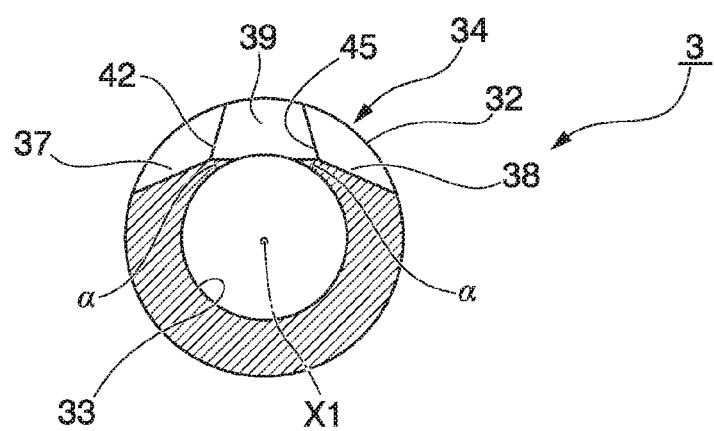
FIG. 12 is a cross-sectional view taken along line F-F of FIG. 5.
Figure 13:
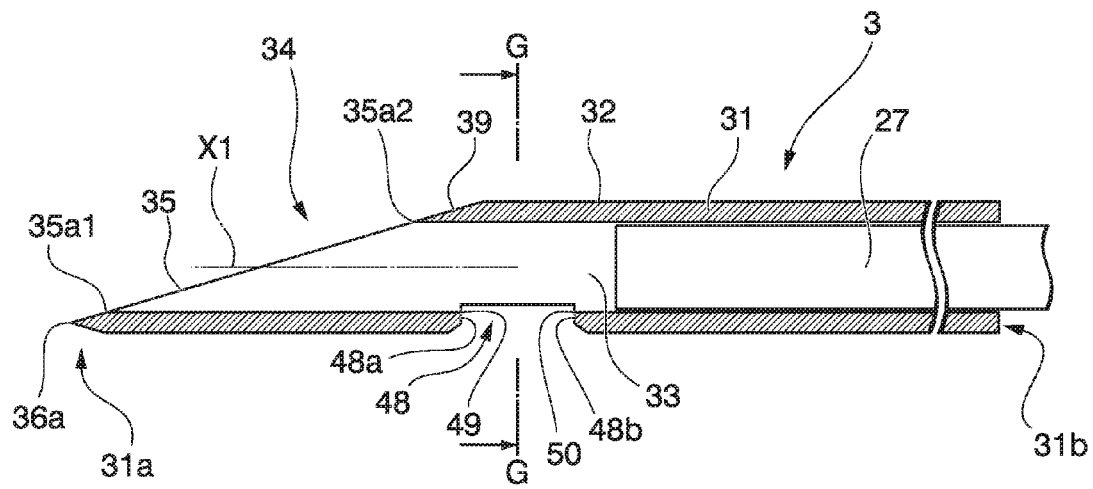
FIG. 13 is a cross-sectional view taken along line H-H of FIG. 5.
Figure 14:
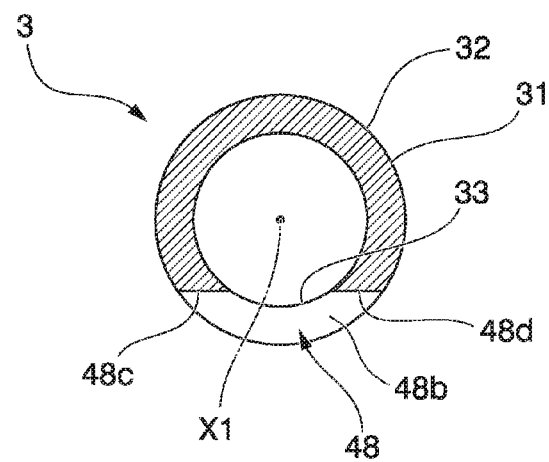
FIG. 14 is a cross-sectional view taken along line G-G of FIG. 13.

FIG. 4 is a perspective view showing the needle tube of the biopsy needle 1. FIG. 5 is a plan view of the needle tube. FIG. 6 is a front view of the needle tube. FIG. 7 is a cross-sectional view taken along line A-A of FIG. 5. FIG. 8 is a cross-sectional view taken along line B-B of FIG. 5. FIG. 9 is a cross-sectional view taken along line C-C of FIG. 5. FIG. 10 is a cross-sectional view taken along line D-D of FIG. 5. FIG. 11 is a cross-sectional view taken along line E-E of FIG. 5. FIG. 12 is a cross-sectional view taken along line F-F of FIG. 5. FIG. 13 is a cross-sectional view taken along line H-H of FIG. 5. FIG. 14 is a cross-sectional view taken along line G-G of FIG. 13.

As shown in FIG. 4, the needle tube 3 includes a tubular section 31 and a needle tip section 34. The needle tube 3 is manipulated to advance and retract in the sheath 7 by the manipulation section 8. The needle tip section 34 of the needle tube 3 can protrude and withdraw from an opening of the distal portion of the sheath 7.

The tubular section 31 has a hollow tubular shape having an outer circumferential surface 32 and an inner circumferential surface 33. The tubular section 31 has a first end portion 31a in a tube axis X1 direction and a second end portion 31b opposite thereto. The needle tip section 34 is formed at the first end portion 31a in the tube axis X1 direction of the tubular section 31. The manipulation section 8 (to be described below) is attached to the second end portion 31b in the tube axis X1 direction of the tubular section 31.

The tubular section 31 is flexible and has elasticity so as to be easily returned to a straight state when it is bent by an external force. For example, the material of the tubular section 31 may be an alloy material such as a stainless steel alloy, a nickel titanium alloy, a cobalt chromium alloy, or the like.

In the embodiment, the first end portion 31a of the tubular section 31 is a distal end that punctures the tissue upon use of a puncture needle 1. Further, the second end portion 31b of the tubular section 31 is a proximal end disposed near an operator's hand together with the manipulation section 8 upon use of the puncture needle 1.

As shown in FIGS. 4 to 6, the needle tip section 34 is formed to be sharp enough for the needle tube 3 to puncture the tissue, and has an opening portion 35 to suction the tissue into the needle tube 3.

The needle tip section 34 includes a plurality of beveled surfaces (a first beveled surface 36, a second beveled surface 37, a third beveled surface 38 and a fourth beveled surface 39) configured to define a contour 35a of the opening portion 35. In addition, the needle tip section 34 includes a first boundary line 40 having a linear shape serving as a boundary between the first beveled surface 36 and the second beveled surface 37, and a second boundary line 43 having a linear shape serving as a boundary between the first beveled surface 36 and the third beveled surface 38.

The opening portion 35 of the needle tip section 34 comes in communication with the outside of the needle tube 3 and the inside of the needle tube 3. The opening portion 35 includes a first opening end portion 35a1 that constitutes the contour 35a of the opening portion 35 at a position closest to the first end portion 31a in the tube axis X1 direction of the tubular section 31, and a second opening end portion 35a2 that constitutes the contour 35a of the opening portion 35 at a position closest to the second end portion 31b in the tube axis X1 direction of the tubular section 31.

The first beveled surface 36 defines a portion constituted of a plane extended in a direction crossing the tube axis X1 of the tubular section 31 and including the first opening end portion 35a1 in the contour 35a of the opening portion 35. In addition, the first beveled surface 36 includes an insertion end 36a configured for insertion of the needle tube 3 into the tissue.

As shown in FIG. 6, the second beveled surface 37 forms an angle with the first beveled surface 36 and is adjacent to the first beveled surface 36. Further, as shown in FIG. 9, the second beveled surface 37 is constituted of a plane adjacent to the inner circumferential surface 33 of the tubular section 31, and a nodal line (a first nodal line 41) to the inner circumferential surface 33 defines a part of the contour 35a of the opening portion 35.

As shown in FIG. 9, in a cross section perpendicular to the tube axis X1 of the tubular section 31, an angle formed between the second beveled surface 37 and the inner circumferential surface 33 is an angle $\theta1$ formed between a tangential line La of the inner circumferential surface 33 and the second beveled surface 37 at an intersection point Pa between the cross section and the first nodal line 41.

In a cross-section perpendicular to the tube axis X1 of the tubular section 31 through a middle point M (see FIG. 5) of a line segment that connects the first opening end portion 35a1 and the second opening end portion 35a2, the angle $\theta1$ formed between the second beveled surface 37 and the inner circumferential surface 33 is less than 90°. In particular, in the embodiment, in a cross section crossing the first nodal line 41 between the second beveled surface 37 and the inner circumferential surface 33 in the cross section perpendicular to the tube axis X1 of the tubular section 31, an angle formed between the second beveled surface 37 and the inner circumferential surface 33 is constantly less than 90°. For this reason, a region including the first nodal line 41 functions as a blade that can cut the tissue open.

As shown in FIG. 6, the third beveled surface 38 forms an angle with the first beveled surface 36 at an opposite side of the second beveled surface 37 with the opening portion 35 sandwiched therebetween and is adjacent to the first beveled surface 36. Further, as shown in FIG. 9, the third beveled surface 38 is constituted of a plane adjacent to the inner circumferential surface 33 of the tubular section 31. A nodal line (a second nodal line 44) of the third beveled surface 38 to the inner circumferential surface 33 of the tubular section 31 defines a part of the contour 35a of the opening portion 35.

As shown in FIG. 9, in a cross section perpendicular to the tube axis X1 of the tubular section 31, an angle formed between the third beveled surface 38 and the inner circumferential surface 33 is an angle θ2 formed between a tangential line Lb of the inner circumferential surface 33 and the third beveled surface 38 at an intersection point Pb between the cross section and the second nodal line 44.

In a cross section perpendicular to the tube axis X1 of the tubular section 31 through the middle point M (see FIG. 5) of the line segment that connects the first opening end portion 35a1 and the second opening end portion 35a2, the angle θ2 formed between the third beveled surface 38 and the inner circumferential surface 33 is less than 90°. In particular, in the embodiment, in a cross section crossing the second nodal line 44 between the third beveled surface 38 and the inner circumferential surface 33 in the cross section perpendicular to the tube axis X1 of the tubular section 31, an angle formed between the third beveled surface 38 and the inner circumferential surface 33 is constantly less than 90°. For this reason, a region including the second nodal line 44 functions as a blade that can cut the tissue open.

As shown in FIGS. 4 to 6, the first boundary line 40 and the second boundary line 43 are non-parallel straight lines having an interval that gradually increases in a direction from the second end portion 31b toward the first end portion 31a in the tube axis X1 direction of the tubular section 31.

As shown in FIGS. 5 and 6, the fourth beveled surface 39 is constituted of a plane adjacent to the second beveled surface 37 and the third beveled surface 38 and disposed between the second beveled surface 37 and the third beveled surface 38. A nodal line 42 between the fourth beveled surface 39 and the second beveled surface 37 is a straight line coaxial with the first boundary line 40 shown in FIG. 5. A nodal line 45 between the fourth beveled surface 39 and the third beveled surface 38 is a straight line coaxial with the second boundary line 43 shown in FIG. 5. The fourth beveled surface 39 defines a portion including the second opening end portion 35a2 in the contour 35a of the opening portion 35 at a position closer to the second end portion 31b than the first beveled surface 36.

In addition, the needle tip section 34 of the biopsy needle 1 of the embodiment undergoes back-cut processing to be inclined from the insertion end 36a toward an opposite side of the first beveled surface 36. As shown in FIG. 6, surfaces (a fifth beveled surface 46 and a sixth beveled surface 47) formed through the back-cut processing are formed at the needle tip section 34 of the biopsy needle 1. As the fifth beveled surface 46 and the sixth beveled surface 47 are formed at the needle tip section 34, the insertion end 36a of the needle tip section 34 becomes an intersection point of three planes of the first beveled surface 36, the fifth beveled surface 46 and the sixth beveled surface 47. For this reason, in the embodiment, puncture performance when the insertion end 36a punctures the tissue is high. Further, when the back-cut processing is performed as described in the embodiment, the insertion end 36a cannot easily pierce the inner wall of the channel 107 in a process in which the needle tip section 34 passes through the bent section of the channel 107 of the endoscope.

Further, the back-cut processing may be not performed on the needle tip section 34.

In addition, further, as shown in FIGS. 13 and 14, the needle tube 3 of the biopsy needle 1 of the embodiment may have a side hole section 48 in which a substantially rectangular through-hole is formed to come in communication with the inside and the outside of the tubular section 31.

As the above-mentioned side hole section 48 is provided, the tissue captured from the opening portion 35 can be hooked by an edge of the side hole section 48 so that it does not easily fall out, or a collected tissue amount can be further increased by further capturing the tissue in the tubular section 31 via the side hole section 48.

Further, a shape of the opening of the side hole section 48 is not limited to a substantially rectangular shape but a shape of the opening may be a circular shape. In addition, the side hole section 48 may not come in communication with the inside and the outside of the tubular section 31 but may be a concave section formed to be recessed with respect to the inner circumferential surface 33 of the tubular section 31.

Figure 15:
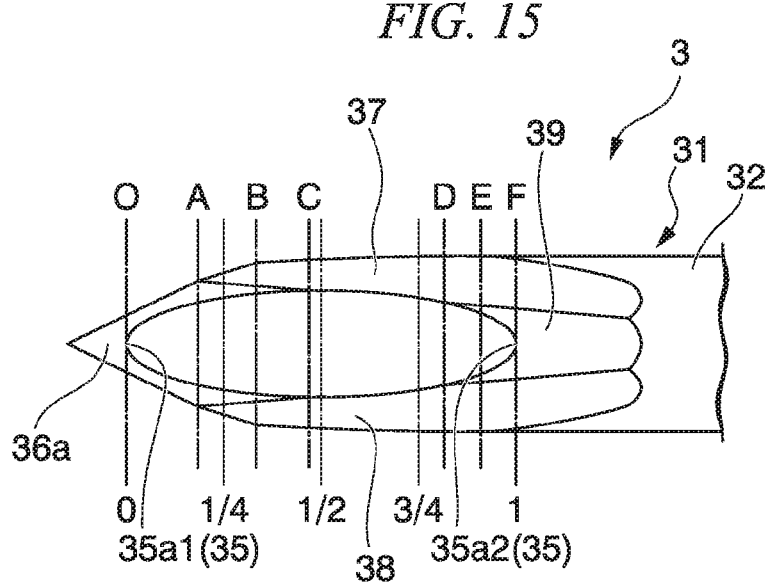
FIG. 15 is a plan view of the needle tube.
Figure 16:
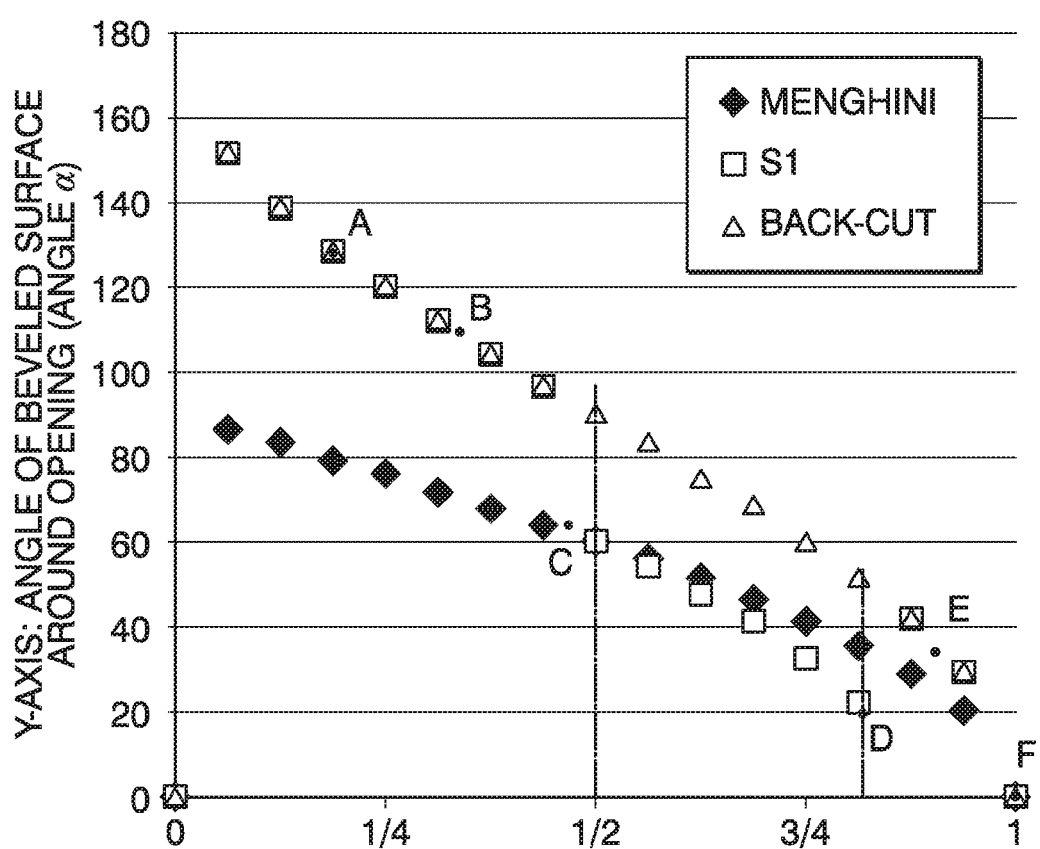
FIG. 16 is a graph showing a blade angle of the needle tube and a blade angle of another known needle tube.

Next, a structure of the needle tip section 34 of the embodiment will be described in more detail in comparison with the known Menghini needle and a needle in the related art in which a tube is simply cut obliquely. FIG. 15 is a plan view of the needle tube 3. FIG. 16 is a graph showing a blade angle of the needle tube 3 and a blade angle of another known needle tube.

FIG. 16 shows an angle (hereinafter referred to as "a blade angle α," see FIGS. 7 to 12) formed between the inner circumferential surface 33 of the tubular section 31 and another surface adjacent to the inner circumferential surface 33 in the cross section perpendicular to the tube axis X1 of the needle tube 3. A horizontal axis in FIG. 16 represents a position of the cross section in the tube axis X1 direction when a position of the second opening end portion 35a2 is 1 using a position of the first opening end portion 35a1 as an origin in the tube axis X1 direction. A vertical axis represents the blade angle α at each position.

In FIG. 16, □ relates to the biopsy needle 1 of the embodiment, ♦ relates to the Menghini needle, and Δ relates a needle on which back-cut processing is performed simply by diagonal cutting. □, ♦ and Δ in FIG. 16 represent the blade angles α obtained by equally dividing a space between an origin (0) in the tube axis X1 direction and a position (1) of the second opening end portion 35a2 into 16 regions. In addition, in FIG. 16, ● represents the blade angles α at positions O, A, B, C, D, E and F in the tube axis X1 direction of the biopsy needle 1 of the embodiment.

The positions O, A, B, C, D, E and F (see FIGS. 5 and 15) in the tube axis X1 direction of the biopsy needle 1 are positions defined as follows.

The position O is a position of a cross section including the first opening end portion 35a1.

The position A is a position of a cross section including an end closest to the first end portion 31a in the first boundary line 40 and the second boundary line 43. At the position A, the blade angle α is defined by the inner circumferential surface 33 and the first beveled surface 36.

The position B is a position of a cross section including the inner circumferential surface 33, the first beveled surface 36, the second beveled surface 37 and the third beveled surface 38. At the position B, the blade angle α is defined by the inner circumferential surface 33 and the first beveled surface 36.

The position C is a position of a cross section including an end closest to the second end portion 31b in the first boundary line 40 and the second boundary line 43. At the position C, each of the blade angles α is defined by the inner circumferential surface 33 and the second beveled surface 37, or the inner circumferential surface 33 and the third beveled surface 38.

The position D is a position of a cross section including an intersection point between the inner circumferential surface 33, the second beveled surface 37 and the fourth beveled surface 39, and an intersection point between the inner circumferential surface 33, the third beveled surface 38 and the fourth beveled surface 39. At the position D, each of the blade angles α is defined by the inner circumferential surface 33 and the second beveled surface 37, or the inner circumferential surface 33 and the third beveled surface 38.

The position E is a position of a cross section including the inner circumferential surface 33, the second beveled surface 37, the third beveled surface 38 and the fourth beveled surface 39. At the position E, the blade angle α is defined by the inner circumferential surface 33 and the fourth beveled surface 39.

The position F is a position of a cross section including the second opening end portion 35a2.

As shown in FIG. 16, in a region from the position C to the position D in the biopsy needle 1 of the embodiment, the blade angle α is smaller than that of the needle formed by simple diagonal cutting. The blade angle α (FIGS. 9 and 10) in the region from the position C to the position D in the biopsy needle 1 of the embodiment has substantially the same configuration as that of the Menghini needle. The position C is a position closer to the first end portion 31a than a middle point between the first opening end portion 35a1 and the second opening end portion 35a2 in a tube axis X1 direction. Here, in the biopsy needle 1 of the embodiment, the opening portion 35 has a contour shape that forms a generally oval shape such that the width thereof is gradually reduced from a middle point between the first opening end portion 35a1 and the second opening end portion 35a2 toward the second end portion 31b.

The blade angle α at the position C in the biopsy needle 1 of the embodiment is less than 90°, and the blade angle α at the middle point between the first opening end portion 35a1 and the second opening end portion 35a2 in the tube axis X1 direction is also less than 90°.

Further, the middle point between the first opening end portion 35a1 and the second opening end portion 35a2 is disposed in a range in which the nodal line (the first nodal line 41) between the second beveled surface 37 and the inner circumferential surface 33 of the tubular section 31 and the nodal line (the second nodal line 44) between the third beveled surface 38 and the inner circumferential surface 33 of the tubular section 31 are formed (between the position C and the position D) in the tube axis X1 direction.

In this way, in an intermediate region (including the position C and the middle point M) of the needle tip section 34 of the embodiment in which the blade angle α of the needle obtained by simply obliquely cutting a tube is about 90°, the blade angle α is less than 90°, in particular, in the embodiment, less than 70° (more specifically, about 60°, substantially equal to the Menghini needle). That is, a blade having an action of cutting the tissue open to substantially the same or a greater extent than the Menghini needle is formed at the needle tip section 34 of the embodiment from the position C to the position F. Further, in the region from the position D to the position F, as shown in FIG. 16, while the blade angle α (see FIGS. 11 and 12) is larger than that in the case of the Menghini needle, since the blade angle α from the position D to the position F is sufficiently smaller than 90°, the blade angle α is sufficient for performing an action of cutting the tissue open.

The rest of configuration of the biopsy needle 1 will be described.

As shown in FIG. 3, the sheath 7 is a tubular member into which the needle tube 3 is inserted. The sheath 7 is formed of a resin, a metal, or the like. A distal end of the sheath 7 is opened such that the needle tube 3 can protrude. A proximal end of the sheath 7 is fixed to a distal portion of the manipulation section 8.

As shown in FIG. 3, the manipulation section 8 includes a manipulation main body 9, a sheath adjuster 18 disposed at a distal side of the manipulation main body 9, and a needle slider 23 disposed at a proximal side of the manipulation main body 9.

The manipulation main body 9 is formed of, for example, ABS resin or the like, and has a lumen through which the needle tube 3 and the sheath 7 are inserted. The distal side of the manipulation main body 9 is inserted into the sheath adjuster 18 formed in a tubular shape. The proximal side of the manipulation main body 9 is inserted into the needle slider 23 formed in a tubular shape. The manipulation main body 9 and the sheath adjuster 18, and the manipulation main body 9 and the needle slider 23 can slide in an axial direction while relative rotation around the axis is restricted by grooves, convex sections, or the like (not shown), formed in an outer circumferential surface engaging with each other. A stopper 10 configured to position the needle slider 23 is provided at the manipulation main body 9.

A distal portion of the sheath adjuster 18 can be attached to the ultrasonic endoscope 100.

A concavo-convex portion that enables easy gripping by an operator may be formed at an outer circumferential surface of the distal portion of the sheath adjuster 18.

The needle slider 23 shown in FIG. 3 is a tubular member configured to hold the second end portion 31b (see FIG. 5) of the tubular section 31 of the needle tube 3. The proximal portion (the second end portion 31b side) of the needle tube 3 extends from the proximal end of the sheath 7 shown in FIG. 3 to the inside of the needle slider 23 shown in FIG. 3. The needle slider 23 is connected to the manipulation main body 9 to be movable with respect to the manipulation main body 9.

In the embodiment, a manipulation stroke length of the needle tube 3 by the needle slider 23 is 40 mm or more. Further, the manipulation stroke length of the needle tube 3 by the needle slider 23 is less than 40 mm.

A concavo-convex portion that enables easy gripping by an operator may be formed at an outer circumferential surface of the distal portion of the needle slider 23.

The stylet 27 shown in FIG. 3 is a wire-shaped member having a knob that can be attached to the needle slider 23 and a cross-sectional shape corresponding to an inner surface shape of the needle tube 3.

Figure 17:
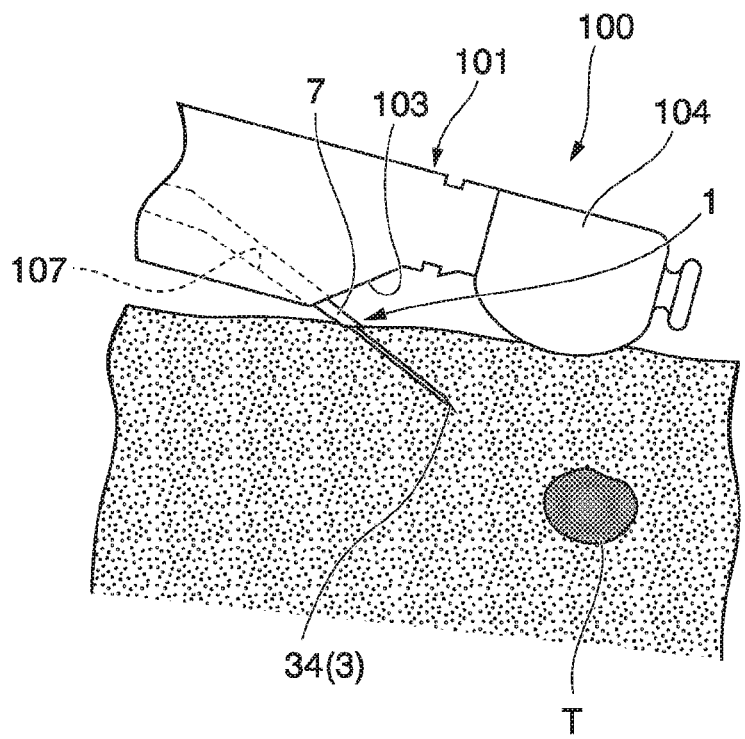
FIG. 17 is a view for describing an action of the biopsy needle.
Figure 18:
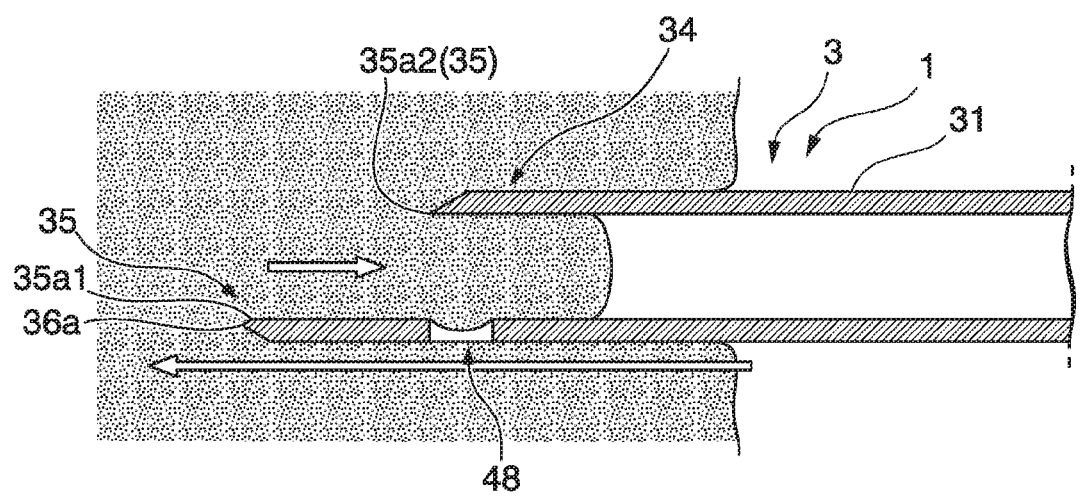
FIG. 18 is a schematic view showing a process of performing a biopsy on tissue using the needle tube.
Figure 19:
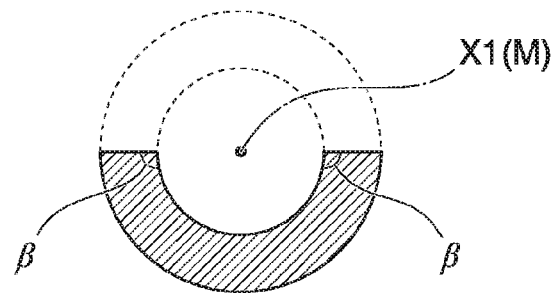
FIG. 19 is a schematic view showing a cross section perpendicular to a tube axis of a known needle tube.
Figure 20:
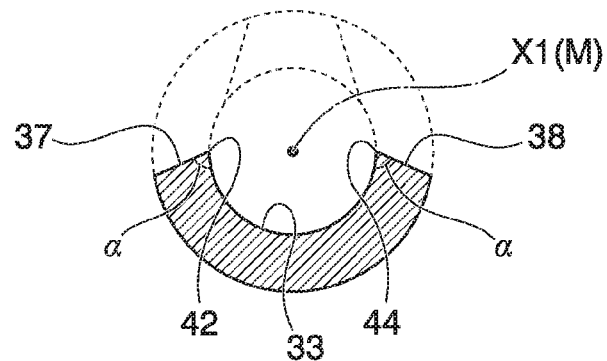
FIG. 20 is a schematic view showing a cross section perpendicular to a tube axis of the needle tube of the embodiment.
Figure 21:
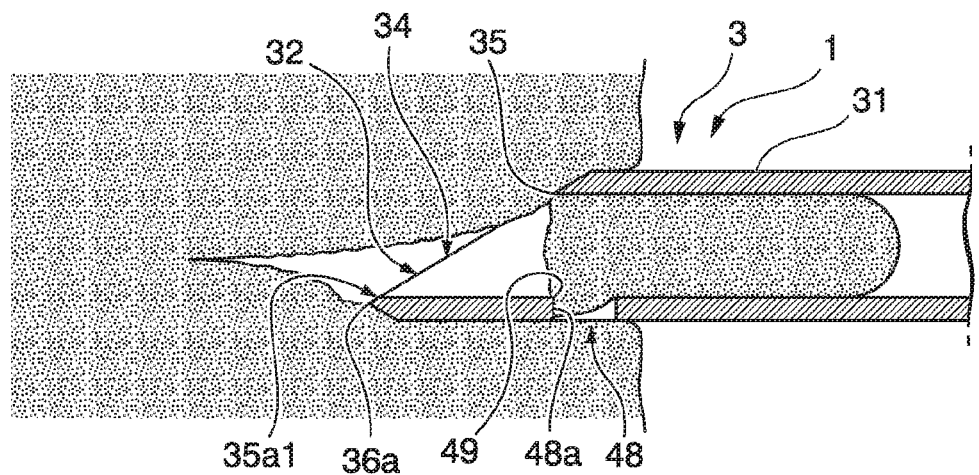
FIG. 21 is a schematic view showing a process of performing a biopsy on the tissue using the needle tube.

An action of the biopsy needle 1 of the embodiment will be described. FIG. 17 is a view for describing an action of the biopsy needle 1. FIG. 18 is a schematic view showing a process of performing a biopsy on the tissue using the needle tube 3. FIG. 19 is a schematic view showing a cross section perpendicular to a tube axis of a known needle tube. FIG. 20 is a schematic view showing a cross section perpendicular to the tube axis X1 of the needle tube 3 of the embodiment. FIG. 21 is a schematic view showing a process of performing a biopsy on the tissue using the needle tube 3.

As shown in FIG. 17, the biopsy needle 1 of the embodiment is inserted into tissue T of the biopsy target in a state in which the needle tip section 34 of the needle tube 3 protrudes from the sheath 7. In a process in which the needle tip section 34 of the needle tube 3 is inserted into the tissue, first, the insertion end 36a (FIG. 4) of the needle tube 3 pierces the tissue, and a nodal line portion between the outer circumferential surface 32 of the tubular section 31 and the first beveled surface 36 cuts the tissue open.

When the needle tube 3 is further inserted into the tissue after the insertion end 36a of the needle tube 3 pierces the tissue as shown in FIG. 18, the nodal line (the first nodal line 41) between the second beveled surface 37 and the inner circumferential surface 33 of the tubular section 31 and the nodal line (the second nodal line 44) between the third beveled surface 38 and the inner circumferential surface 33 of the tubular section 31 shown in FIG. 4 come in contact with the tissue. In the embodiment, since the region including the first nodal line 41 and the second nodal line 44 functions as a blade that can cut the tissue open, the tissue is cut open at the position of the first nodal line 41 and the second nodal line 44 and divided into a tissue piece guided into the tubular section 31 and a tissue piece remaining outside the tubular section 31. For this reason, as shown in FIG. 18, when the needle tube 3 is inserted into the tissue, the tissue piece is guided into the tubular section 31 while being cut away in a substantially columnar shape.

FIG. 19 shows a cross section of the needle tube obtained by simply cutting a tube obliquely and perpendicular to the tube axis passing a point corresponding to the middle point M shown in FIG. 5. In the above-mentioned needle tube in the related art, a blade angle (designated by reference numeral β in FIG. 19) corresponding to the blade angle α in the embodiment is larger than the blade angle α shown in FIG. 20. Since a portion of the needle tube 3 having a small blade angle can easily intrude into the tissue, the needle tube 3 of the embodiment has better performance of cutting the tissue open in the vicinity of the middle point M than the needle tube in the related art obtained by simply cutting the tube obliquely.

After the needle tube 3 is inserted into the tissue, the tissue is further captured in the tubular section 31 by suction. For example, a suction apparatus or the like (not shown) may be connected to the proximal side of the biopsy needle 1, and suction through the biopsy needle 1 using the suction apparatus or the like becomes possible. Here, in comparison with the needle tube in the related art obtained by simply cutting the tube obliquely, since the needle tube 3 of the embodiment has a wide range of a sharp blade surface (the blade angle α is less than 90°, more preferably, less than 70°) at the proximal side of the middle point, a larger amount of tissue can be excised. The excised tissue can be securely captured in the tubular section 31 by suction.

When the needle tube 3 is pulled back to the second end portion 31b side, the needle tube 3 can be pulled out of the tissue in a state in which a portion of the tissue is held in the tubular section 31 as shown in FIG. 21. As the biopsy needle 1 is removed to the outside of the body in a state in which the portion of the tissue is held in the tubular section 31, the tissue of the biopsy target can be collected.

As described above, in the embodiment, since the second beveled surface 37 and the third beveled surface 38 are formed such that the tissue can be cut open at the positions of the first nodal line 41 and the second nodal line 44, incision that allows the tissue to be introduced into the tubular section 31 can be performed by an insertion operation of the needle tube 3.

In addition, in comparison with the needle tube in the related art obtained by simply cutting the tube obliquely, a sharp blade surface (the blade angle α is less than 90°, more preferably less than 70°, and further preferably about 60°, substantially equal to the Menghini needle) configured to cut the tissue open can be formed within a wide range. In particular, the blade surface can be formed within a wide range at the proximal side of the opening portion of the needle tube.

In addition, in the embodiment, since all of the first beveled surface 36, the second beveled surface 37, the third beveled surface 38 and the fourth beveled surface 39 are planes, machining of forming the needle tip section 34 can be easily performed without machining the entire circumference like the Menghini needle in the related art. As a result, the biopsy needle of the embodiment has high producibility.

Hereinabove, while the embodiment of the present invention has been described in detail with reference to the accompanying drawings, a specific configuration is not limited to the embodiment but may include design changes and so on without departing from the spirit of the present invention.

While preferred embodiments of the present invention have been described, the present invention is not limited to the embodiments. Additions, omissions, substitutions, and other variations may be made to the present invention without departing from the spirit and scope of the present invention. The present invention is not limited by the above description, but by the appended claims.

What is claimed is:

1. A biopsy needle comprising:
   a tubular section formed in a hollow tube shape and having a first end portion in a tube axis direction and a second end portion opposite thereto; and
   a needle tip section having an opening portion in communication with the inside of the tubular section and formed at a position including the first end portion of the tubular section,
   wherein the needle tip section includes:
      a first beveled surface constituted of a plane extended in a direction crossing a tube axis of the tubular section and configured to define a part of a contour of the opening portion;
      a second beveled surface adjacent to the first beveled surface and forming an angle with the first beveled surface, constituted of a plane adjacent to an inner circumferential surface of the tubular section, and configured to define a part of the contour of the opening portion using a nodal line between the inner circumferential surface and the second beveled surface;
      a third beveled surface adjacent to the first beveled surface and forming an angle with the first beveled surface at an opposite side of the second beveled surface with the opening portion interposed therebetween, constituted of a plane adjacent to the inner circumferential surface of the tubular section, and configured to define a part of the contour of the opening portion using a nodal line between the inner circumferential surface and the third beveled surface;
      a first boundary line serving as a boundary between the first beveled surface and the second beveled surface; and
      a second boundary line serving as a boundary between the first beveled surface and the third beveled surface, and
   the first boundary line and the second boundary line are non-parallel straight lines having an interval that gradually increases in a direction from the second end portion toward the first end portion in the tube axis direction of the tubular section.

2. The biopsy needle according to claim 1, wherein, in a cross section crossing the nodal line between the second beveled surface and the inner circumferential surface and perpendicular to the tube axis of the tubular section, an angle formed between the second beveled surface and the inner circumferential surface is constantly less than 90°, and in a cross section crossing the nodal line between the third beveled surface and the inner circumferential surface and perpendicular to the tube axis of the tubular section, an angle formed between the third beveled surface and the inner circumferential surface is constantly less than 90°.

3. The biopsy needle according to claim 2, wherein the opening portion includes:

a first opening end portion that configures the contour of the opening portion at a position closest to the first end portion in the tube axis direction of the tubular section; and a second opening end portion that configures the contour of the opening portion at a position closest to the second end portion in the tube axis direction of the tubular section, and a cross section perpendicular to the tube axis of the tubular section through a middle point of a line segment that connects the first opening end portion and the second opening end portion crosses the nodal line between the second beveled surface and the inner circumferential surface and the nodal line between the third beveled surface and the inner circumferential surface.

4. The biopsy needle according to claim 3, wherein, in the cross section perpendicular to the tube axis of the tubular section through the middle point of the line segment that connects the first opening end portion and the second opening end portion, the angle formed between the second beveled surface and the inner circumferential surface is less than 70°, and in the cross section perpendicular to the tube axis of the tubular section through the middle point of the line segment that connects the first opening end portion and the second opening end portion, the angle formed between the third beveled surface and the inner circumferential surface is less than 70°.

5. The biopsy needle according to claim 4, wherein, in the cross section crossing the nodal line between the second beveled surface and the inner circumferential surface and perpendicular to the tube axis of the tubular section, the angle formed between the second beveled surface and the inner circumferential surface is constantly less than 70°, and in the cross section crossing the nodal line between the third beveled surface and the inner circumferential surface and perpendicular to the tube axis of the tubular section, the angle formed between the third beveled surface and the inner circumferential surface is constantly less than 70°.

6. The biopsy needle according to claim 1, further comprising a fourth beveled surface constituted of a plane configured to define a part of the contour of the opening portion at a position closer to the second end portion than the first beveled surface, adjacent to the second beveled surface and the third beveled surface, and disposed between the second beveled surface and the third beveled surface.

7. The biopsy needle according to claim 1, wherein the needle tip section has a side hole formed at an outer circumferential surface of the tubular section of an opposite side of the first beveled surface and in communication with the inside of the tubular section.

* * * * *